United States Patent
Hickey

[11] Patent Number: 5,645,607
[45] Date of Patent: Jul. 8, 1997

[54] HIP STEM PROVISIONAL HAVING ADJUSTABLE NECK OFFSETS

[75] Inventor: Paul Francis Hickey, Leesburg, Ind.

[73] Assignee: Zimmer, Inc., Warsaw, Ind.

[21] Appl. No.: 399,107

[22] Filed: Mar. 2, 1995

[51] Int. Cl.$^6$ ........................................... A61F 2/36
[52] U.S. Cl. ............................................. 623/23
[58] Field of Search ........................... 623/16, 18, 19, 623/21, 22, 23

[56] References Cited

U.S. PATENT DOCUMENTS

| | | | |
|---|---|---|---|
| 3,685,058 | 8/1972 | Tronzo. | |
| 4,676,797 | 6/1987 | Anapliotis et al. | 623/18 |
| 4,834,758 | 5/1989 | Lane et al. | 623/18 |
| 4,963,155 | 10/1990 | Lazzeri et al. | 623/23 |
| 4,985,037 | 1/1991 | Petersen | 623/20 |
| 5,002,581 | 3/1991 | Paxson et al. | 623/23 |
| 5,133,760 | 7/1992 | Petersen et al. | 623/20 |
| 5,135,529 | 8/1992 | Paxson et al. | 606/85 |
| 5,201,882 | 4/1993 | Paxson | 623/23 |
| 5,261,915 | 11/1993 | Durlacher et al. | 606/85 |
| 5,275,603 | 1/1994 | Ferrante et aql. | 606/86 |
| 5,290,313 | 3/1994 | Heldreth | 623/20 |
| 5,336,268 | 8/1994 | Rispeter | 623/23 |

FOREIGN PATENT DOCUMENTS

| | | | |
|---|---|---|---|
| 0547354 | 6/1993 | European Pat. Off. | 623/23 |
| 0549480 | 6/1993 | European Pat. Off. | 623/22 |
| 2640497 | 6/1990 | France | 623/22 |
| 3600804 | 8/1987 | Germany | 623/23 |
| 9418911 | 9/1994 | WIPO | 623/23 |

OTHER PUBLICATIONS

Hip Systems—PP A20, A24, A31, A125, Zimmer 1993 Catalog.

*Primary Examiner*—Mary Beth Jones
*Attorney, Agent, or Firm*—Margaret L. Geringer

[57] ABSTRACT

A hip stem provisional 10 having adjustable neck offsets is disclosed. Hip stem provisional 10 includes a stem part 12 and an attachable cone provisional 20. Cone provisional 20 includes a base 30 and a neck 40 shiftably connected to the base. Base 30 has a mounting surface 36 upon which neck 40 is shiftably seated. Neck 40 can be positioned along the length of mounting surface 36 at a plurality of discrete positions. In one embodiment of cone provisional 20, base 30 has an arcuate mounting surface 36, which allows neck 40 to be positioned along the length of the mounting surface at a plurality of discrete positions, each having a different neck offset and neck angle. In a second embodiment of the cone provisional 60, the base 70 has a flat mounting surface 76, which allows the neck 80 to be positioned along the length of the mounting surface at a plurality of discrete positions, each having a different neck offset, but having a fixed neck angle.

17 Claims, 4 Drawing Sheets

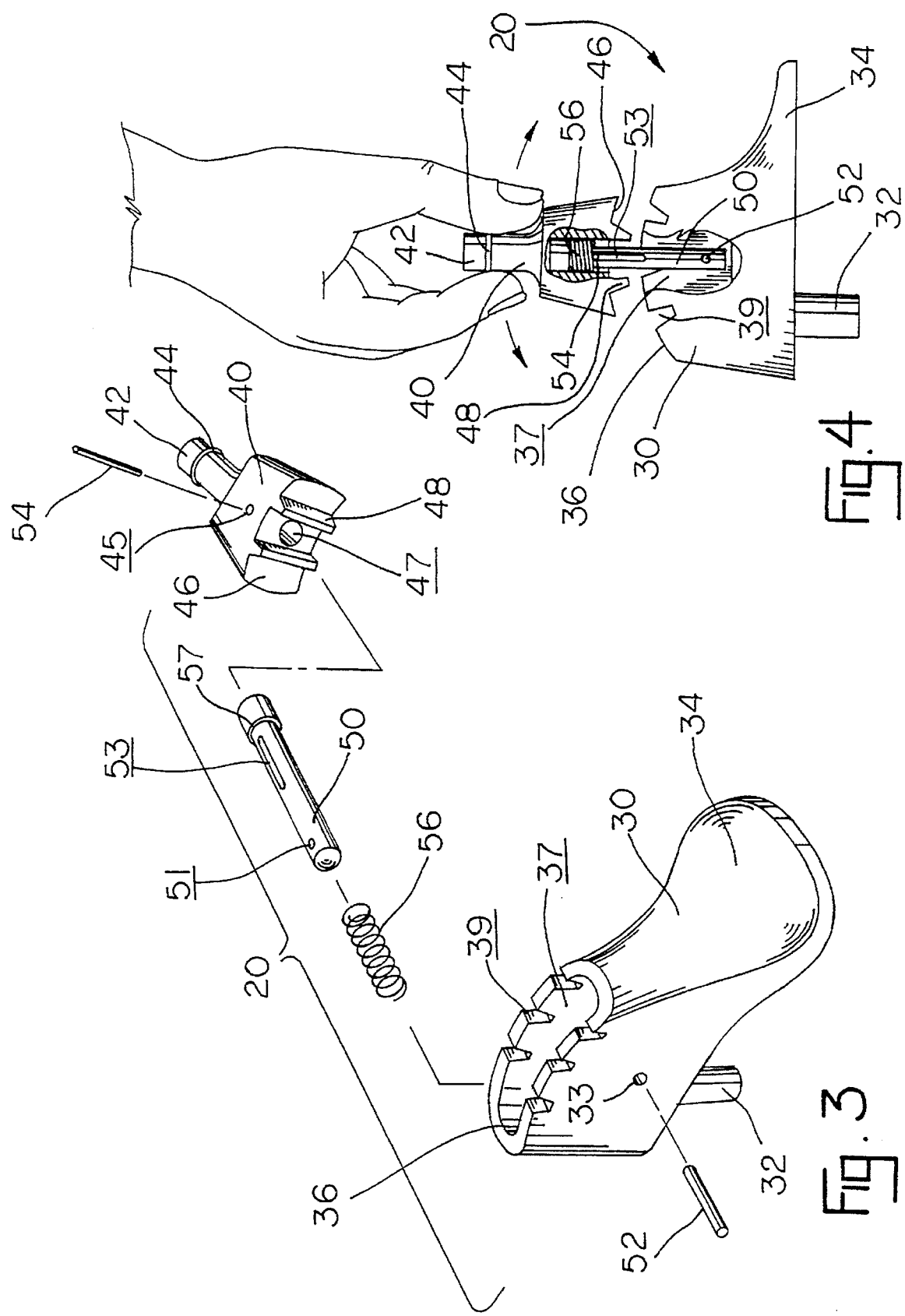

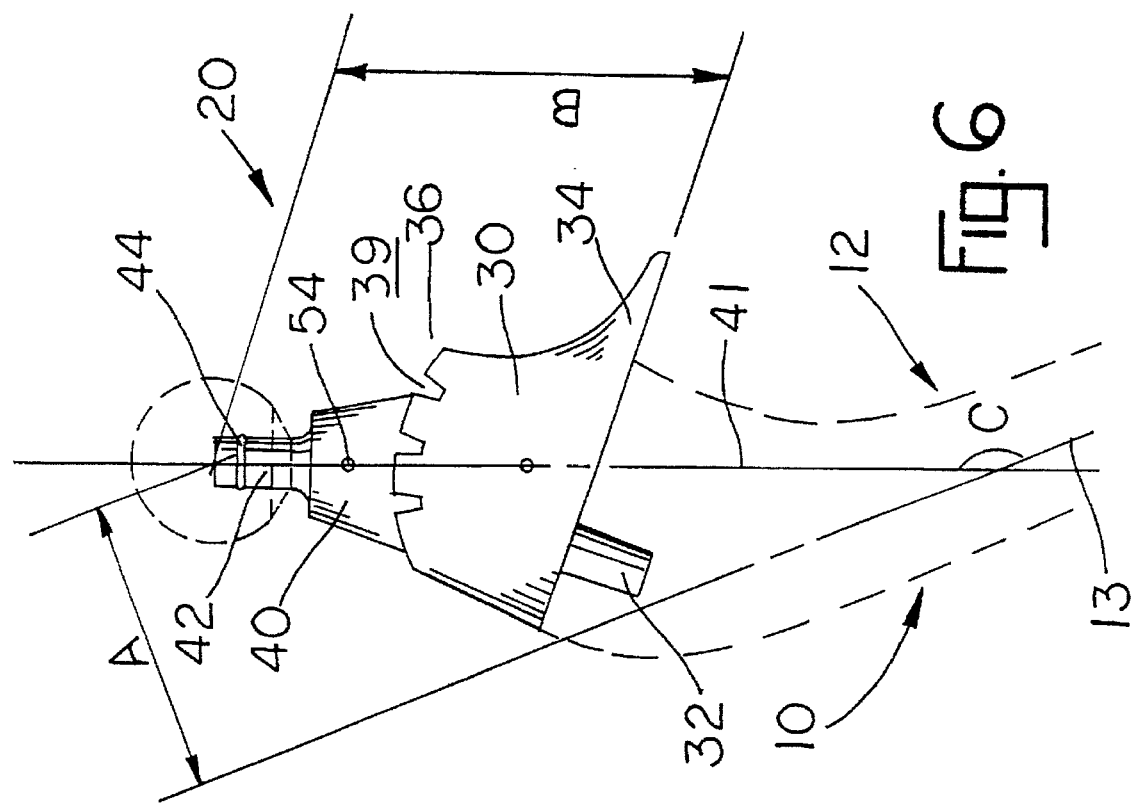
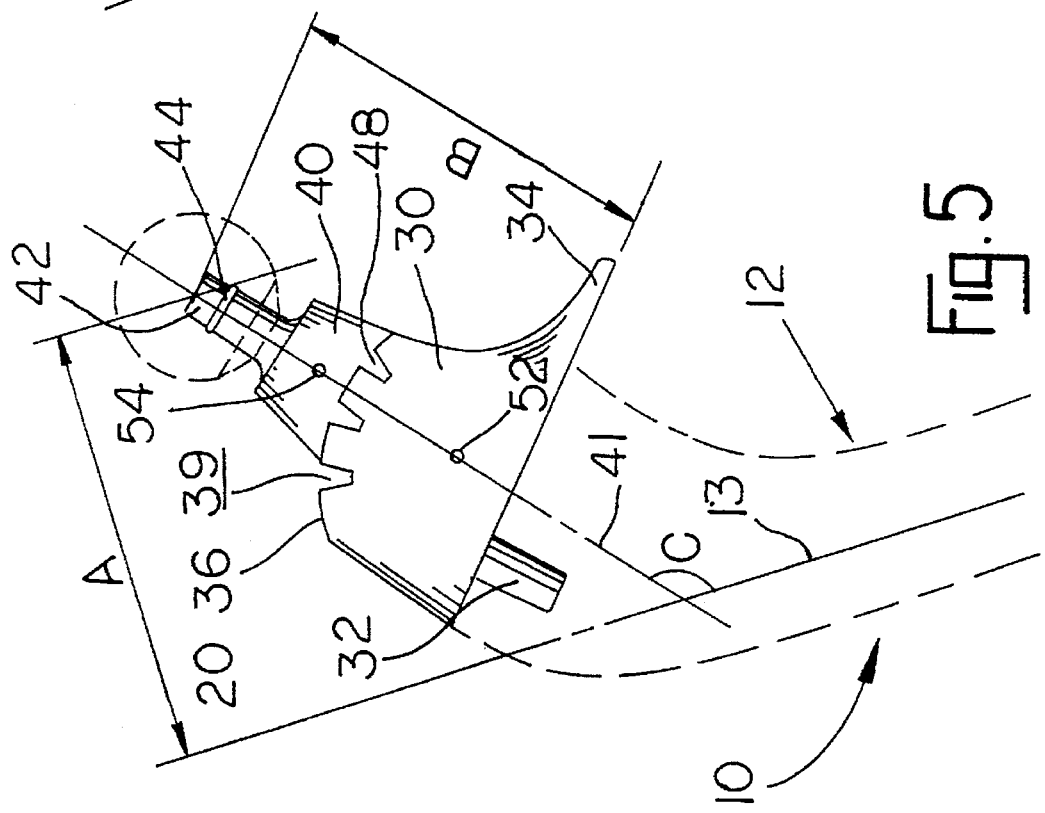

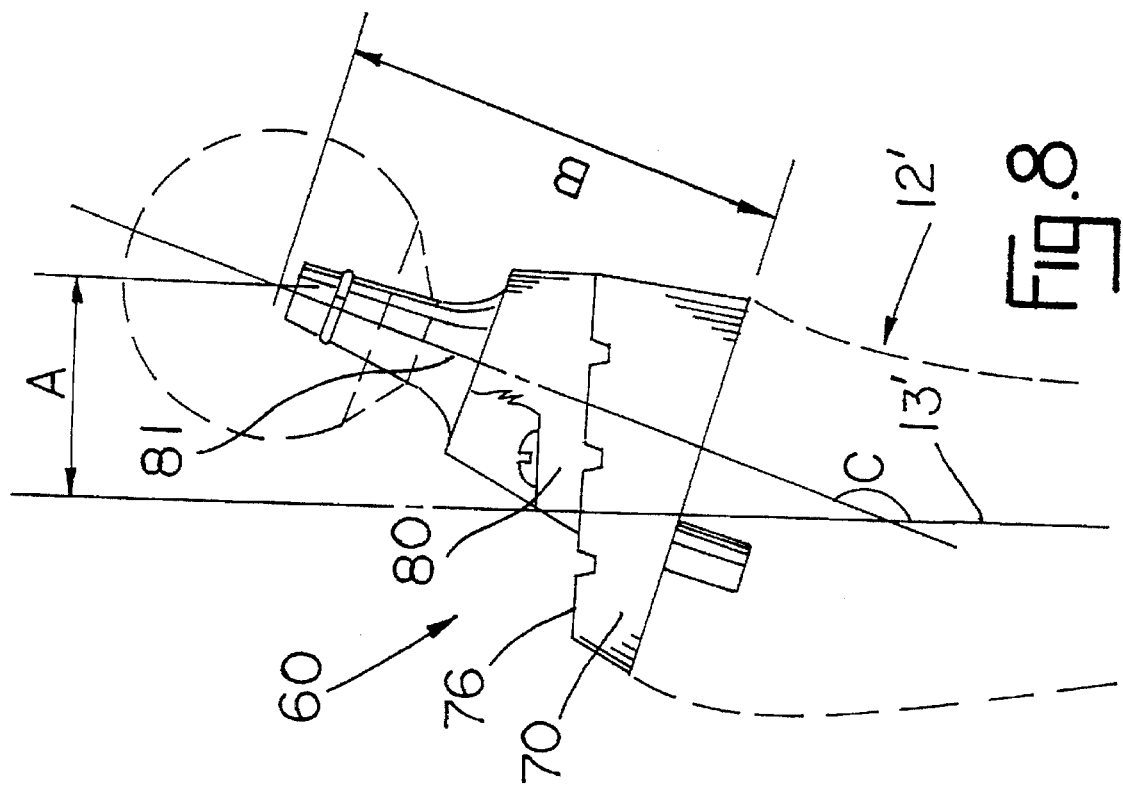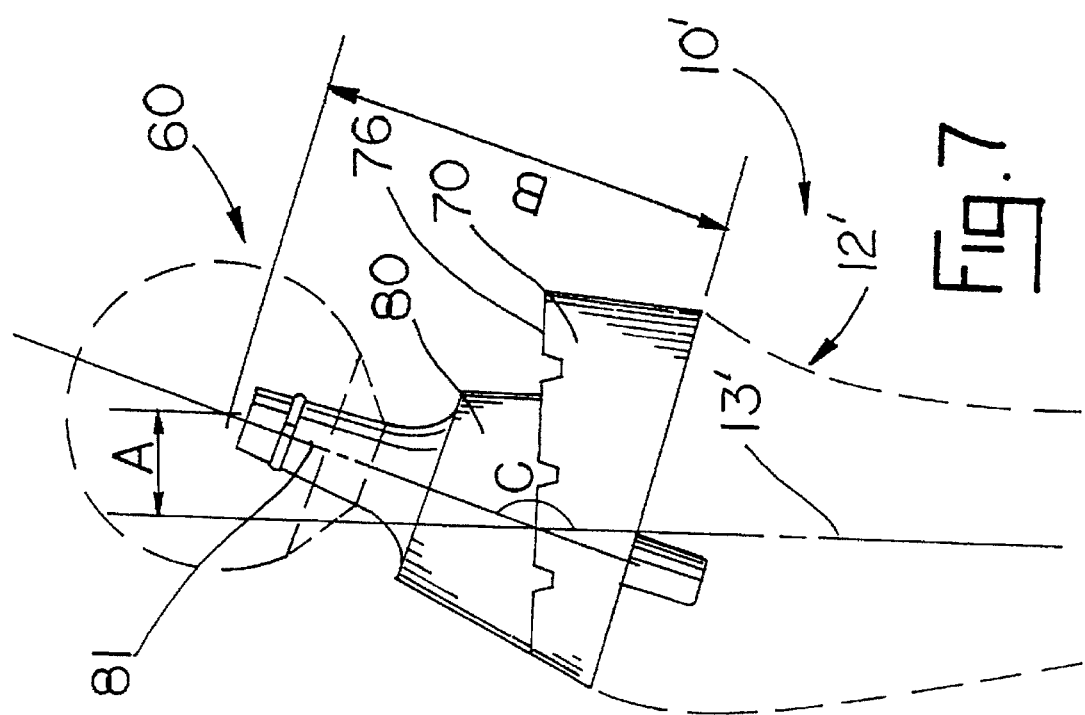

HIP STEM PROVISIONAL HAVING ADJUSTABLE NECK OFFSETS

This invention relates to a hip stem provisional, and in particular a hip stem provisional having adjustable neck offsets.

BACKGROUND OF THE INVENTION

In joint replacement surgery, provisional or trial components are used to select the proper joint prosthesis. The provisional components are temporarily installed to ensure proper sizing, placement and orientation of the joint prosthesis and to anatomically orient the prothesis to the joint. In hip arthroplasty, hip stem provisionals are used to select the proper hip stem prosthesis. Modular hip stem provisionals have been developed that include a provisional stem or rasp and a trochanteral attachment, known as a cone provisional. Cone provisionals include a neck which is used to support a femoral head provisional. In the medical arts, the orientation of the neck in relation to the stem shaft or rasp is described in terms of neck offset, neck length, neck angle, and anteversion. These terms are well known in the medical field. Since the orientation of the femoral neck varies among patients, multiple cone provisionals are required for each fitting. The use of multiple cone provisional attachments greatly increases the instrument count of the surgical procedure; therefore, it is advantageous to have a single cone provisional that can accommodate multiple neck orientations.

U.S. Pat. No. 5,336,268 granted Aug. 9, 1994, to Rispeter discloses a femoral stem and a prosthesis head which includes an adjusting device, locking devices that fix the adjusting device, and a link element guided in a stationary link area. A joint head, having a supporting body, is held on the link element and is adjustable with respect to the link area via an intermediate plate. A tension element penetrates the adjusting device and fixes the locking devices with respect to one another.

U.S. Pat. No. 5,002,581 granted Mar. 26, 1991, to Paxson et al. discloses a hip stem prosthesis that includes a trochanteral attachment having an adjustable anteversion. The trochanteral attachment includes a rotatable neck part, which can be selectively rotated to adjust the anteversion of the neck with respect to the attachment's base.

SUMMARY OF THE INVENTION

The hip stem provisional of this invention includes a stem part and an attachable cone provisional, which accommodates adjustable neck offsets at fixed or varying neck angles and neck lengths. The cone provisional includes a base having a proximal mounting surface upon which the neck is shiftably seated. The neck can be positioned along the length of the mounting surface at a plurality of discrete offset positions. The neck is shiftably connected to the base by a pivot rod and held against the base by a spring. The pivot rod and spring allows the neck to be manually pulled from the base to allow for repositioning. The base has three parallel channels equally spaced across the mounting surface. The neck includes two parallel flanges, which are seated in two of the channels formed in the base to secure said neck in one of said offset positions.

In one embodiment, the base has an arcuate mounting surface, upon which the neck is seated. Because of the curvature of the mounting surface, the neck offset and/or neck angle is greater in one position than in another position. The curvature of the mounting surface and the pivot rod's axis of rotation can be selected to provide the desired neck length features. In a second embodiment, the neck is shiftably seated on a flat mounting surface. The flat mounting surface allows the neck to be positioned along the length of the surface at a plurality of discrete neck offsets at a fixed neck angle. While both embodiments of this invention are illustrated using modular hip provisionals including a separate stem part and cone provisional, the teaching of this invention can be incorporated into a single stem component, where the base and stem part are integrally formed, with the adjustable neck portion adjustably seated thereon. In addition, the teachings may be incorporated into implant components as well as provisional components.

Accordingly, an advantage of this invention is to reduce the need for multiple hip stem provisional components to accommodate varying neck offsets, angles and lengths.

Another advantage of this invention is to provide a hip stem prosthesis including a neck which can be secured at a plurality of discrete positions relative to the stem's longitudinal axis.

Another advantage of this invention is to provide for a cone provisional attachable to a hip stem component which accommodates a variety of neck offsets at fixed or variable neck angles and lengths.

Other advantages will become apparent upon a reading of the following description.

BRIEF DESCRIPTION OF THE DRAWINGS

A preferred embodiment of the invention has been depicted for illustrative purposes only wherein:

FIG. 3 is an exploded view of the cone provisional of FIG. 2;

FIG. 4 is a side view of the cone provisional of FIG. 2 illustrating the pivotal adjustment of the neck;

FIG. 5 is a side view of the cone provisional showing the neck in one position;

FIG. 6 is a side view of the cone provisional showing the neck in a second position;

FIG. 7 is a side view of a second embodiment of the cone provisional of this invention showing the neck in one position; and FIG. 8 is a side view of the cone provisional of FIG. 7 showing the neck in a second position.

DESCRIPTION OF THE PREFERRED EMBODIMENT

The preferred embodiments herein described are not intended to be exhaustive or to limit the invention to the precise form disclosed. They are chosen and described to explain the principles of the invention and its application and practical use to enable others skilled in the art to utilize its teachings.

Figure 2:
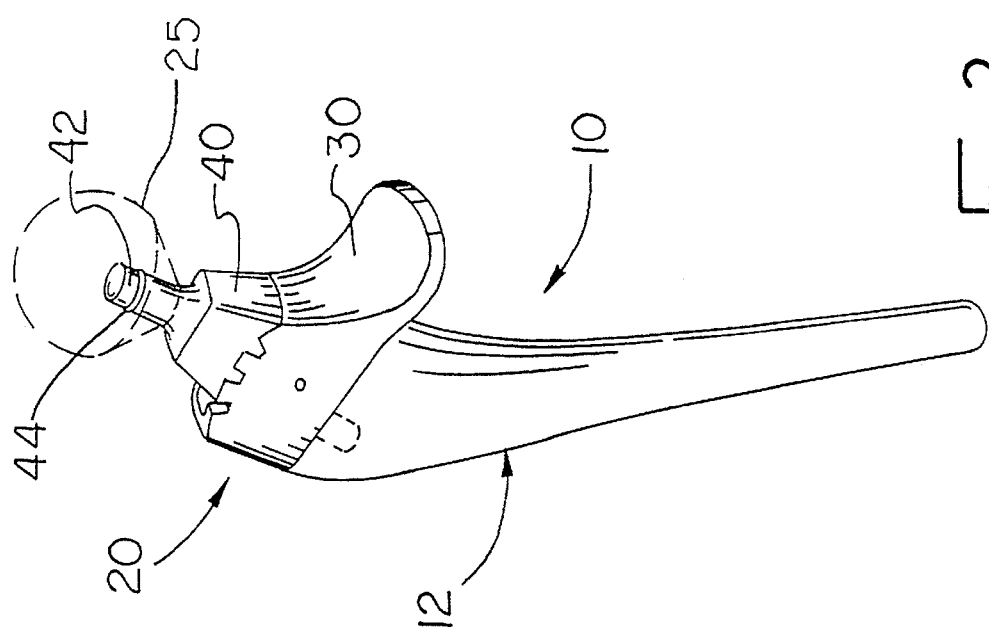
FIG. 2 is a perspective view of the hip stem provisional of this invention showing one embodiment of the cone provisional.
Figure 1:
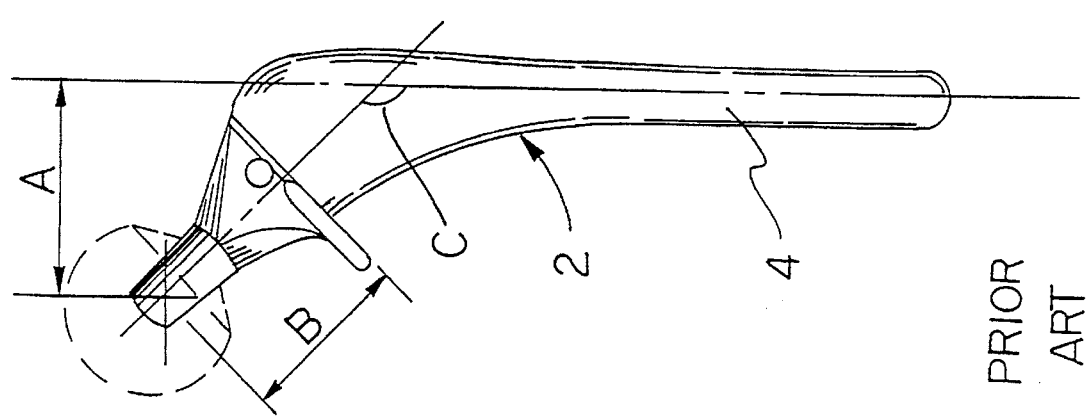
FIG. 1 is side view of a conventional hip stem illustrating the conventions of neck offset, length and angle.

FIG. 1 shows a conventional hip stem 2 for the purpose of illustrating the conventions of neck offset, neck length and neck angle. The terms, neck offset, length, angle, and anteversion, are well known and understood in the medical field. Hip stem 2 includes a stem part 4 and an integral neck 6. As shown, neck offset (A) is the distance from the longitudinal axis of the stem shaft to the center of the femoral head. Neck length (B) is the distance measured along the neck's longitudinal axis from the center of the head to the bottom of the collar on a collared prosthesis or to the osteotomy line on a collarless prosthesis (i.e. where the prosthesis would sit on the bone). The neck angle (C) is the angle formed by the intersection of the neck's longitudinal axis and the stem shaft's longitudinal axis. It is noted that an alternate definition for neck length is the distance measured along the neck's longitudinal axis from the center of the head to the neck axis and stem axis intersection. This alternate definition for neck length is not called out on the Figs., but is noted for reference.

FIGS. 2–6 show one embodiment of a modular hip stem provisional 10 of this invention. Provisional 10 includes a stem part 12 and cone provisional 20. The stem part 12 may also be used as the stem portion of a rasp for forming the proper sized opening in the femoral canal as is known in the art, although no rasp teeth are illustrated on stem part 12. Stem part 12 includes an elongated body having a longitudinal axis 13. Cone provisional 20 includes a base 30 and a shiftable neck 40, which is configured to support a provisional femoral head (not shown).

Base 30 is connected to the proximal end of stem part 12 by a mounting post 32 which is fitted into a bore in the stem part. In this embodiment, base 30 includes a collar 34, which is used to seat hip provisional 10 against the femur bone. Collared, as well as collarless, cone provisionals are well known in the orthopedic field. As shown in FIG. 3, base 30 has an arcuate mounting surface 36, upon which neck 40 is seated. A longitudinal slot 37 is defined in mounting surface 36, which runs substantially the length of the mounting surface. Three equally spaced parallel channels 39 are formed laterally across mounting surface 36.

Neck 40 has a longitudinal axis 41 and terminates in an end portion 42. An annular recess is defined in end portion 42 of neck 40 to receive a resilient C-shaped clip or snap ring 44. The snap ring 44 may be used to secure the provisional femoral head 25 (shown in phantom lines) to neck 40. End 42 can be slightly tapered or cylindrical, as desired, to provide a mating fit with a femoral head having a correspondingly shaped hole in the head for interconnection therewith. Neck 40 has an arcuate surface 46, which is complimentary to mounting surface 36 of base 30. A perpendicular bore 47 extends into neck part 40 from neck surface 46. Two parallel flanges 48 extend across neck surface 46 on either side of bore 47. Flanges 48 are spaced at a distance equal to the spacing of channels 39. In addition, the cross sections of flanges 48 are complimentary to the cross sections of channels 39. It is noted that a single flange could be provided, if desired.

As best shown in FIGS. 3 and 4, neck 40 is shiftably connected to base 30 by a pivot rod 50 and held against the base by a spring 56. One end of rod 50 is pivotally connected within slot 33 by a pivot pin 52, which extends through aligned bores 33, 51 in base 30 and rod 50. The other end of rod 50 is extensibly connected within bore 45 by a pin 54, which extends through a bore 47 in neck part 40 and a longitudinal slot 53 in rod 50. Spring 56 is journaled about rod 50 and seated between pin 54 and an annular shoulder 57 at the end of rod 50. The tension of spring 56 holds neck 40 against base 30.

As shown in FIGS. 5–6, neck 40 can be secured at two discrete positions along the length of mounting surface 36 to provide two different neck offsets (A). It is noted that additional channnels 39 could be provided, in order to provide additional discrete positions, and thus more than two different neck offsets. At each neck position, flanges 48 are seated within channels 39 to secure neck 40 at each position. As shown in FIG. 4, manually pulling neck 40 away from base 30 disengages ribs 48 from channels 39 to allow the neck to be repositioned along mounting surface 36. As shown, the neck offset (A) is greater when neck 40 is positioned as in FIG. 5 than when neck 40 is positioned as in FIG. 6. Because of the curvature of mounting surface 36, the neck angle (C) changes as neck 40 is shifted between positions. The curvature of mounting surface 36 and the position of pivot pin 52, as well as the position or spacing of the channels 39 and flanges 48 can be selected to provide the desired neck length features.

FIGS. 7 and 8 show a second embodimemt of a cone provisional 60 used with a rasp stem 12'. Cone provisional 60 includes a trochanteral base 70 and neck 80 similar to cone provisional 20 of FIGS. 2–6; however, neck 80 is shiftably seated on a flat mounting surface 76, which is perpendicular to the longitudinal axis 13' of stem shaft 12'. As in the first embodiment, neck 80 can be positioned at two discrete positions along the length of mounting surface 76 to provide two distinct neck offset positions; however, the neck angle remains constant at each neck position because mounting surface 76 is flat. It is noted that mounting surface 76, as shown in FIGS. 7–8, is not parallel to the bottom flat surface of base 70, however, it could be, if desired. Also, since the mounting surface 76 is flat the shiftable connection between the different positions must be by a mechanism other than the pivoting connection shown in FIG. 4 for the embodiment of FIGS. 2–6. Thus, a suitable interconnecting means which allows the neck 80 to lift and slide along base 70 may be used to selectively secure neck 80 to base 70 in the different positions. Alternatively, a screw in cone provisional 60 may be screwed into one of a plurality of screw holes (not shown) in the base 70 to secure the neck 80 in the desired position. However, any suitable connection may be utilized.

While both embodiments of this invention are illustrated using modular hip provisionals including a separate stem part and cone provisional, the teaching of this invention can be incorporated into a single stem component including the adjustable neck portion thereon. For example, the base of each cone provisional can be formed as part of the stem part itself. In addition, the teachings may be incorporated into implant components as well as provisional components. It is understood that the above description does not limit the invention to the details given, but may be modified within the scope of the following claims.

I claim:

1. A hip stem provisional comprising:.

a base part located on said stem provisional and including an elongated mounting surface, a neck part extending outwardly from said base part, and means for shiftably connecting said neck part to said base part for shiftable movement along said mounting surface between a first position and second position to provide at least two different selectable discrete neck offsets, and wherein said neck part is nonrotatably, shiftably connected to said base part along said mounting surface at a first angular orientation when said neck part is in its said first position and at a second angular orientation, different from said first angular orientation, when said neck part is in its said second position.

2. The provisional of claim 1 wherein said mounting surface is arcuate.

3. A hip stem provisional comprising:

a base part located on said stem provisional and including an elongated mounting surface, a neck part extending outwardly from said base part, and means for shiftably connecting said neck part to said base part for shiftable movement along said mounting surface between a first position and second position to provide at least two different selectable discrete neck offsets, and wherein said connecting means includes a rod part having one end interconnected to said base part and the other end connected to said neck part to permit transverse movement of said neck part along said mounting surface between its said first position and said second position.

4. The provisional of claim 3 wherein said base part has a slot defined longitudinally in said mounting surface, said rod one end is pivotally connected to said base within said slot for radial movement along the length of said slot.

5. The cone provisional of claim 3 wherein said neck part is connected to said other rod end for extensible movement about said other rod end toward and away from said mounting surface, said connecting means also includes spring means for holding said neck surface against said mounting face.

6. The provisional of claim 3 wherein the base part which is located on the stem provisional is separately formed from the stem provisional, and is connectable thereto.

7. The provisional of claim 6 wherein said neck part is shiftably connected to said base part along said mounting surface at a constant angular orientation with respect to said base part at each said first and second positions.

8. The provisional of claim 7 wherein said mounting surface is substantially planar.

9. A hip stem provisional comprising:

a base part located on said stem provisional and including an elongated mounting surface, a neck part extending outwardly from said base part, and means for shiftably connecting said neck part to said base part for shiftable movement along said mounting surface between a first position and second position to provide at least two different selectable discrete neck offsets, and wherein said mounting surface has at least two channels defined therein, said neck part has a surface overlying said mounting surface, said neck surface includes a flange selectively seated within one of said channels to secure said neck part to said base part in one of said first position and said second position.

10. A modular hip joint prosthesis comprising:

a stem part having a longitudinal axis and terminating in opposite proximal and distal ends, said proximal end having an elongated mounting surface, a neck part extending outwardly from said stem proximal end, and means for shiftably connecting said neck part to said base part for shiftable movement along said mounting surface between a first position and second position to provide at least two different selectable discrete neck offsets, and wherein said neck part is nonrotatably, shiftably connected to said base part along said mounting surface at a first angular orientation when said neck part is in its said first position and at a second angular orientation, different from said first angular orientation, when said neck part is in its said second position.

11. The prosthesis of claim 10 wherein said mounting surface is arcuate.

12. A modular hip joint prosthesis comprising:

a stem part having a longitudinal axis and terminating in opposite proximal and distal ends, said proximal end having an elongated mounting surface, a neck part extending outwardly from said stem proximal end, and means for shiftably connecting said neck part to said base part for shiftable movement along said mounting surface between a first position and second position to provide at least two different selectable discrete neck offsets, and wherein said connecting means includes a rod part having one end interconnected to said base part and the other end connected to said neck part to permit transverse movement of said neck part along said mounting surface between its said first position and said second position.

13. The prosthesis of claim 12 wherein said base part has a slot defined longitudinally in said mounting surface, said rod one end is pivotally connected to said base within said slot for radial movement along the length of said slot.

14. The prosthesis of claim 12 wherein said neck part is connected to said other rod end for extensible movement about said other rod end toward and away from said mounting surface, said connecting means also includes spring means for holding said neck surface against said mounting face.

15. A modular hip joint prosthesis comprising:

a stem part having a longitudinal axis and terminating in opposite proximal and distal ends, said proximal end having an elongated mounting surface, a neck part extending outwardly from said stem proximal end, and means for shiftably connecting said neck part to said base part for shiftable movement along said mounting surface between a first position and second position to provide at least two different selectable discrete neck offsets, and wherein said mounting surface has at least two channels defined therein, said neck part has a surface overlying said mounting surface, said neck surface includes a flange selectively seated within one of said channels to secure said neck part to said base part in one of said first position and said second position.

16. The prosthesis of claim 15 wherein said neck part is shiftably connected to said base part along said mounting surface at a constant angular orientation with respect to said base part at each said first and second positions.

17. The prosthesis of claim 16 wherein said mounting surface is substantially planar.

* * * * *